United States Patent [19]

Schinski et al.

[11] 4,289,701

[45] Sep. 15, 1981

[54] LACTONE SUBSTITUTED ANILINE PREPARATION

[75] Inventors: William L. Schinski, San Rafael; Francis J. Freenor, III, Richmond, both of Calif.

[73] Assignee: Chevron Research, San Francisco, Calif.

[21] Appl. No.: 93,765

[22] Filed: Nov. 13, 1979

[51] Int. Cl.$^3$ .......................................... C07D 307/30
[52] U.S. Cl. .................................................. 260/343.6
[58] Field of Search ..................................... 260/343.6

[56] References Cited

U.S. PATENT DOCUMENTS 2,530,348  11/1946  Britton et al. ................ 260/343.6
3,933,860  1/1976   Chan ............................. 260/343.5
4,165,322  8/1979   Reynolds, Jr. .................. 260/343.6

FOREIGN PATENT DOCUMENTS 659483  10/1951  United Kingdom ............. 260/343.6

*Primary Examiner*—Alan L. Rotman
*Assistant Examiner*—Jane T. Fan
*Attorney, Agent, or Firm*—D. A. Newell; T. G. DeJonghe

[57] ABSTRACT

A process for preparing a lactone-substituted aniline, preferably in one reaction vessel, which comprises contacting a 2,4-dihalobutyric acid with an aniline reactant and subsequently adding an inorganic base to the reaction vessel.

10 Claims, No Drawings

LACTONE SUBSTITUTED ANILINE PREPARATION

BACKGROUND OF THE INVENTION

The present invention relates to a process for making a lactone-substituted aniline. The compounds prepared in accordance with the present invention are useful in fungicides or as materials for preparing fungicides such as those fungicides described in Chan U.S. Pat. No. 3,933,860.

J. D. Cleveland, commonly assigned patent application U.S. Ser. No. 45,369, titled "Lactone Preparation by Cyclization" discloses preparation of lactones by cyclization of 2,4-dibromo-butyric acid.

R. N. Reynolds, commonly assigned patent application U.S. Ser. No. 928,481, titled "Alkylation of Aniline with a Lactone in the Presence of a Base" discloses the preparation of lactone-substituted anilines by reaction of an aniline with a halo-substituted lacone in the presence of a base.

SUMMARY OF THE INVENTION

We have found that good yields of a lactone-substituted aniline can be obtained by a reaction sequence that may be carried out in one reaction vessel by reacting a 2,4-dihalobutyric acid with an aniline reactant.

In accordance with the present invention a process is provided for making a compound of the formula:

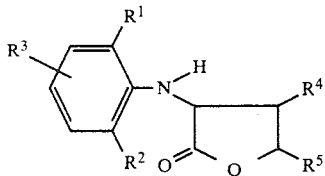

in an overall reaction which process comprises contacting a compound of the formula:

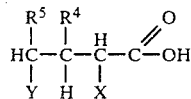

with a compound of the formula:

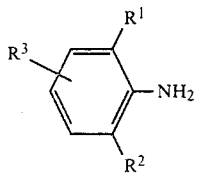

in a reaction zone at a temperature between 20° and 250° C. to obtain a reaction mixture and then contacting said reaction mixture with an inorganic base at a temperature between 20° C. and 250° C. in a second part of the overall reaction to thereby obtain the compound of formula I, wherein $R^1$ is lower alkyl or hydrogen;

$R^2$ is lower alkyl or hydrogen;

$R^3$ is lower alkyl, hydrogen, $C_1$-$C_4$ alkoxy, $C_1$-$C_4$ halo alkyl, trifluoromethyl, nitro, or halo;

$R^4$ is lower alkyl, hydrogen, or $C_1$-$C_4$ alkoxy;

$R^5$ is lower alkyl or hydrogen; and

Y and X are halo.

Preferably the overall reaction is carried out in one reaction vessel.

Among other factors the present invention is based on our finding that good yields of a lactone-substituted aniline are obtained in a method wherein (1) a 2,4-dihalobutyric acid and an aniline reactant are fed to a reaction vessel, preferably under anhydrous conditions; and (2) after an initial reaction period, an aqueous base is added to the reaction vessel at a rate to maintain the pH below 7. A key factor in the present invention is the finding that dimethyl aniline can be used as the sole base for a first part of the overall reaction.

The overall reaction of the present invention is believed to proceed in two parts. In the first part a cyclization reaction is believed to occur wherein the butyric acid is cyclized to a lactone with simultaneous formation of an aniline hydrohalide salt. In the second part this lactone is used to alkylate the aniline by displacing one of the hydrogen atoms on the nitrogen of the aniline. It was found that in the first part of the reaction there evidently is not a substantial loss of yield due to byproduct formation from reaction of the aniline reactant with the primary (4-position) halo-substituted end of the dihalobutyric acid.

The pH used in the second part of the process of the present invention is acidic, for example, between 0.1 and 7.0. Preferably the pH is maintained between 0.5 and 4.0 and more preferably between 0.5 and 2.5. During the second part of the overall reaction preferably an inorganic base (preferably in the form of an aqueous solution) is added to the reaction zone sufficiently slowly to maintain the desired acidic pH.

Suitable inorganic bases for the second part of the process of the present invention include alkali hydroxides or carbonates. The alkali may be an alkaline earth metal that is, Ca or Ba; or an alkali metal, that is, Li, Na, K, Rb, or Cs. Preferred bases are the milder bases such as the alkali metal or alkaline earth metal carbonates, especially sodium carbonate and calcium carbonate and sodium or calcium bicarbonate. Sodium carbonate has been found to be an especially effective inorganic base for the process of the present invention. The inorganic bases are preferably dissolved in water at concentrations ranging from 5% to saturated.

The temperature during the reaction is preferably maintained between 20° and 250° C. The reaction is exothermic and thus provides its own heat to accelerate the reaction. Preferably the temperature is maintained between 20° and 40° during the first part of the reaction and between 95° and 110° during the second part of the reaction.

The present invention, of course, offers the important advantage of obtaining a lactone-substituted aniline, starting from an aniline and dihalobutyric acid, using, if desired, only one reaction zone or one reaction vessel rather than two separate reaction zones, one each to carry out cyclization and subsequent alkylation.

The presence of aqueous base during the first step of the process is undesirable and leads to by-product formation and loss of yield. Carrying out the first step in an anhydrous manner gives maximum yield. The exotherm in the first reaction can be used to provide the heat for reaction, but care should be taken to control it.

Preferred substituents for the R, X and Y groups on the aniline and butyric acid reactants are as follows:

$R^1$ is methyl or ethyl

R² is methyl or ethyl
R³ is hydrogen
R⁴ is hydrogen
R⁵ is hydrogen
X is bromo or chloro
Y is bromo or chloro Particularly preferred substitutents for the R, X and Y groups are
R¹ and R² are methyl
R³, R⁴ and R⁵ are hydrogen
X and Y are bromo.

EXAMPLES

Example 1: One-Reactor Process (6517-33)

A three-necked round bottom flask equipped with a stirrer, a thermometer, a dropping funnel, and a condenser was charged with 360 grams (1.46 mols) of 2,4-dibromobutyric acid. This acid was heated to 50° C., and then 161 grams (1.33 mols) of 1,6-dimethylaniline was added dropwise over a period of 30 minutes. The temperature was maintained at 50°–60° C. throughout this addition. A precipitate formed after about 80% of the dimethylaniline was added.

The temperature was then maintained at 105°–110° C. while an aqueous solution of 141 grams (1.33 mols) of sodium carbonate in 400 ml of water was added at a rate so as to maintain the pH of the mixture below 1.5. When all carbonate had been added, the pH rose to about 5. The mixture was cooled to 70° C. and 380 ml of toluene was added. The crude reaction product formed two layers. The lower, aqueous phase was removed. The upper organic phase was washed and then stripped at 110° C. to remove all water. The remaining material weighed 558 grams, and analyzed as 44.4% solids. An aliquot was analyzed and the yield was then calculated as 76.7% of N'-2'-butyrolactone-2,6-dimethylaniline based on dibromobutyric acid.

Example 2: Two-reactor Process (6517-32 B and 6517-37)

A. The same apparatus as before was charged with 360 grams (1.46 mols) of 2,4-dibromobutyric acid. This acid was heated to 50° C. and an aqueous solution of 65.7 grams (0.62 mol) of sodium carbonate in 207 ml of water was added at such a rate as to maintain the pH at or below 1.5. After one hour, the addition was complete. The mixture was cooled and allowed to separate into two layers. The layers were separated. The aqueous layer was extracted twice with methylenedichloride. The combined extracts were stripped of solvent, and the resulting oil was added to the organic layer to give a total of 235 grams of crude 2-bromobutyrolactone. Analysis of the crude product showed it to contain 87% of the desired bromolactone.

B. The same apparatus as in (A) was charged with 230 grams (1.21 mols) of the crude 87% 2-bromobutyrolactone of part (A) and 161 grams (1.33 mols) of 2,6-dimethylaniline. This mixture was heated to 110° C. and stirred at this temperature for one hour. A precipitate formed. Then 70.5 grams (0.665 mol) of sodium carbonate dissolved in 200 ml of water was added at a rate of about 1.2 ml/min. until about two-thirds was added and then at a rate of 0.5 ml/min. until the remainder was added. The resulting mixture was stirred for an additional 30 minutes at 110° C.

The reaction mixture was then cooled and 266 ml of toluene was added. Two phases formed and were separated. The organic phase was extracted with dilute base, dilute acid, and water. The resulting crude product was stripped of water at 110° C. The dry solution weighed 452 grams and analyzed as having 50% solvent. An aliquot of the solvent-free crude product was analyzed and the yield was then calculated as 62.7% of N'-2'-butyrolactone-2,6-dimethylaniline based on dibromobutyric acid.

A comparison of Examples 1 and 2 shows a much higher yield of the desired product by operating in accordance with a preferred embodiment of the present invention, i.e., by using the anhydrous dimethylaniline as a base to effect the first step of the reaction and by adding the inorganic base at a rate sufficient to keep the pH below 7 in the second step of the reaction.

Example 3: One-Reactor Synthesis (6502-15)

A 100-ml three-necked round bottom flask, equipped with a stirrer, thermometer, condenser, and additional funnel was charged with 24.6 grams (0.1 mol) of 2,4-dibromobutyric acid at 55° C. Then 12.1 grams (0.1 mol) of 2,6-dimethylaniline was added slowly over 20 minutes. A precipitate formed. Heated the flask to 100° C. and added 10.6 grams (0.1 mol) of sodium carbonate dissolved in water over a period of about two hours. The resulting mixture was allowed to stand at room temperature for two days.

Workup using dichloromethane to extract the organic material produced 18.8 grams of a crude product analyzing as 69.5% N'-2'-γ-butyrolactone-2,6-dimethylaniline, a 64% yield.

Example 4: One-Reactor Synthesis with pH Control (6499-24)

A 500-ml flask equipped as in Example 3 was charged with 135.26 grams (0.55 mol) of 2,4-dibromobutyric acid at 25° C. Then 60.5 grams (0.5 mol) of 2,6-dimethylaniline was added dropwise with cooling to maintain the temperature between 28° C. and 30° C. A precipitate formed.

Then 53 grams (0.5 mol) of sodium carbonate dissolved in 172 ml of water was added slowly while maintaining the pH at or below about 3.0. After 40 ml had been added, the mixture was heated to a temperature of 110° C. in 80 minutes. This temperature and pH were maintained until all the carbonate solution was added. The reaction mixture was refluxed for an additional 30 minutes.

Workup in the usual way gave 107.6 grams of crude product which analyzed as 69.4% of N'-2'-γ-butyrolactone-2,6-dimethylaniline, a 72.8% yield.

A comparison of Examples 3 and 4 shows that careful control of the pH during the addition of aqueous inorganic carbonate results in better yields of the desired product.

What is claimed is:

1. A process for making

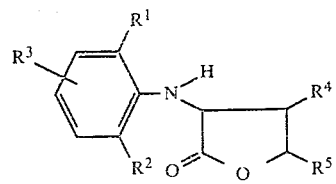

in an overall reaction which comprises contacting

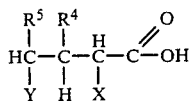

with

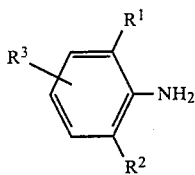

in a reaction zone at a temperature between 20° and 250° C. to obtain a reaction mixture and contacting said reaction mixture with an inorganic base at a temperature between 20° C. and 250° C. in a second part of the overall reaction to thereby obtain the compound of formula I, wherein $R^1$ is lower alkyl or hydrogen;

$R^2$ is lower alkyl or hydrogen;

$R^3$ is lower alkyl, hydrogen, $C_1$–$C_4$ alkoxy, $C_1$–$C_4$ halo alkyl, trifluoromethyl, nitro, or halo;

$R^4$ is lower alkyl, hydrogen, or $C_1$–$C_4$ alkoxy;

$R^5$ is lower alkyl or hydrogen; and

X and Y are halo.

2. A process in accordance with claim 1, wherein the pH is maintained between about 0.1 and 7.0 during the second part of the overall reaction.

3. A process in accordance with claim 2, wherein the base is an alkali metal carbonate.

4. A process in accordance with claim 3, wherein the pH is maintained between 0.5 and 4.0.

5. A process in accordance with claim 1, wherein $R^1$ is methyl or ethyl $R^2$ is methyl or ethyl $R^3$ is hydrogen $R^4$ is hydrogen $R^5$ is hydrogen X is bromo or chloro Y is bromo or chloro.

6. A process in accordance with claim 1, wherein $R^1$ and $R^2$ are methyl $R^3$, $R^4$ and $R^5$ are hydrogen X and Y are bromo.

7. A process in accordance with claim 4, $R^1$ and $R^2$ are methyl $R^3$, $R^4$ and $R^5$ are hydrogen X and Y are bromo.

8. A process in accordance with claim 5, wherein the base is sodium carbonate.

9. A process in accordance with claim 7, wherein the base is sodium carbonate.

10. A process in accordance with claim 9, wherein the same reaction vessel is used for both parts of the overall reaction.

* * * * *